US010682454B2

(12) United States Patent
Coulthard et al.

(10) Patent No.: US 10,682,454 B2
(45) Date of Patent: Jun. 16, 2020

(54) APPARATUS FOR PERFORMING HAEMODIALYSIS

(75) Inventors: Malcolm Coulthard, Newcastle upon Tyne (GB); Michael Whitaker, Newcastle upon Tyne (GB); Clive Griffiths, Newcastle upon Tyne (GB); Michael Drinnan, Newcastle upon Tyne (GB)

(73) Assignee: The Newcastle Upon Tyne Hospitals NHS Foundation Trust, Newcastle upon Tyne (GB)

( * ) Notice: Subject to any disclaimer, the term of this patent is extended or adjusted under 35 U.S.C. 154(b) by 695 days.

(21) Appl. No.: 14/126,666

(22) PCT Filed: Jun. 14, 2012

(86) PCT No.: PCT/GB2012/051368
§ 371 (c)(1),
(2), (4) Date: Dec. 16, 2013

(87) PCT Pub. No.: WO2012/172356
PCT Pub. Date: Dec. 20, 2012

(65) Prior Publication Data
US 2014/0110319 A1    Apr. 24, 2014

(30) Foreign Application Priority Data
Jun. 15, 2011 (GB) .................................. 1110021.1

(51) Int. Cl.
*A61M 1/36* (2006.01)
*A61M 1/30* (2006.01)
*A61M 1/34* (2006.01)
*A61M 1/10* (2006.01)

(52) U.S. Cl.
CPC ............ *A61M 1/3663* (2013.01); *A61M 1/30* (2013.01); *A61M 1/302* (2014.02); *A61M 1/303* (2014.02);
(Continued)

(58) Field of Classification Search
None
See application file for complete search history.

(56) References Cited

U.S. PATENT DOCUMENTS 4,174,637 A    11/1979  Mulzet et al.
4,466,804 A     8/1984  Hino
(Continued)

FOREIGN PATENT DOCUMENTS

EP    0087964    3/1982
EP    1738784    1/2003

OTHER PUBLICATIONS

International Search Report for related PCT Application No. PCT/GB2012/051368, dated Mar. 8, 2013 (4 pages).

*Primary Examiner* — Jonathan M Peo
(74) *Attorney, Agent, or Firm* — Winthrop & Weinstine, P.A.; Nadeem W. Schwen

(57) ABSTRACT

An apparatus for performing haemodialysis on a patient comprises: first blood transfer means (3) for selectively withdrawing blood from a patient and storing it in a first storage portion (5); second blood transfer means (11) for removing filtered blood from a filtration device (7) and storing it in a second storage portion (13); and a fluid measurement system (51a, 51b) for periodically measuring the respective volumes of blood in the first and second storage portions; adding the volume of blood in the first storage portion to the volume of blood in the second storage portion at that time in order to calculate the total volume of blood within the first and second storage portions at that time; and comparing the total measured volumes of blood within the first and second storage portions measured over a predetermined time interval to calculate the volume of fluid removed from the blood during that predetermined time interval.

10 Claims, 4 Drawing Sheets

(52) U.S. Cl.
CPC .............. *A61M 1/308* (2014.02); *A61M 1/34* (2013.01); *A61M 1/3604* (2014.02); *A61M 1/367* (2013.01); *A61M 1/3639* (2013.01); *A61M 1/3643* (2013.01); *A61M 1/3644* (2014.02); *A61M 1/3646* (2014.02); *A61M 1/10* (2013.01); *A61M 1/1006* (2014.02); *A61M 1/1081* (2013.01); *A61M 2205/3331* (2013.01); *A61M 2205/3334* (2013.01); *A61M 2205/3389* (2013.01); *A61M 2205/3396* (2013.01); *A61M 2240/00* (2013.01)

(56) References Cited

U.S. PATENT DOCUMENTS

| | | | | |
|---|---|---|---|---|
| 4,643,714 | A * | 2/1987 | Brose | A61M 1/30 |
| | | | | 128/DIG. 13 |
| 4,885,001 | A * | 12/1989 | Leppert | A61M 1/30 |
| | | | | 128/DIG. 13 |
| 4,897,189 | A * | 1/1990 | Greenwood | A61M 1/30 |
| | | | | 210/195.2 |
| 5,120,303 | A * | 6/1992 | Hombrouckx | A61M 1/30 |
| | | | | 604/506 |
| 7,615,028 | B2 * | 11/2009 | O'Mahony | A61M 1/34 |
| | | | | 210/645 |
| 2001/0034502 | A1 * | 10/2001 | Moberg | A61M 5/1456 |
| | | | | 604/154 |
| 2003/0019276 | A1 | 1/2003 | Ericson et al. | |
| 2005/0205476 | A1 * | 9/2005 | Chevallet | A61M 1/30 |
| | | | | 210/85 |
| 2010/0179467 | A1 | 7/2010 | Gunther et al. | |

\* cited by examiner

APPARATUS FOR PERFORMING HAEMODIALYSIS

CROSS-REFERENCE TO RELATED APPLICATIONS

This application is a national stage entry of International PCT Appl. No. PCT/GB2012/051368, titled Apparatus for Performing Haemodialysis, filed Jun. 14, 2012, which claims priority to United Kingdom patent appl. no. 1110021.1, filed Jun. 15, 2011.

BACKGROUND OF THE INVENTION

The present invention relates to an improved apparatus for performing haemodialysis on a patient suffering from renal failure. Although the present invention can be used to perform haemodialysis on any suitable patient, the present invention is particularly, although not exclusively, suitable for use in performing haemodialysis on a neonate.

Acute renal failure is common in very small preterm babies and can sometimes be secondary to other problems such as hypotension and hypoxia caused by medical or surgical conditions. However, babies having a weight of less than 8 kg are notoriously difficult to dialyse, especially those having a weight as low as 1 kg.

Peritoneal dialysis, whereby the peritoneum in the abdomen of the patient is used as a membrane across which molecules from the blood are passed, as opposed to conventional haemodialysis, can sometimes be an easier method to perform on very small preterm babies. However, it is not always feasible and it does not always efficiently clear the molecules, which can include urea, potassium and phosphates for example, from the blood.

There are two main factors which can make haemodialysis difficult in very small preterm babies: —

A first factor is that the volumes of the extracorporeal circuits typically used in existing haemodialysis apparatuses are large relative to the blood volume of such a baby, necessitating the priming of the extracorporeal circuit with fresh or modified blood. For example, at the time of writing, the typical minimum haemodialysis extracorporeal circuit volume is around 49 ml, which is large in relation to a baby's blood volume of around 85 ml/kg. As a result of this, with conventional haemodialysis apparatus, it is preferable that the extracorporeal circuit be primed with blood for heavier babies, and essential that this is the case with very small preterm babies.

A second factor is that the rate of flow of blood from the access vessels of very small preterm babies is typically very low, resulting in inadequate haemodialysis and/or clotting within the extracorporeal circuit. The reason for this low rate of flow is that the maximum rate of flow of blood through a blood vessel is limited by, inter alia, the diameter of the blood vessel. To elaborate, for laminar flow, the rate of flow of blood can be analysed using Poiseuille's Law which states that the rate of flow of fluid is directly proportional to the pressure gradient multiplied by the fourth power of the radius of the tube through which the fluid flows. It follows that blood can only be extracted from very small babies having very narrow blood vessels at a very low flow rate for acceptable pressure gradients, when compared with larger children having larger blood vessels.

BRIEF SUMMARY OF THE INVENTION

An aim of the present invention is to provide an apparatus which overcomes or at least alleviates the problems associated with known apparatus for performing haemodialysis.

In particular, it is an aim of the present invention to provide an apparatus which reliably and efficiently haemodialyses very small preterm babies.

In accordance with a first aspect of the present invention there is provided an apparatus for performing haemodialysis on a patient, said apparatus comprising: —
  (i) a first blood transfer means for selectively withdrawing blood from a patient and temporarily storing it in a first storage portion;
  (ii) a filtration device through which the blood removed from the patient is passed in order to remove molecules from the blood;
  (iii) a second blood transfer means for selectively removing filtered blood from the filtration device and temporarily storing it in a second storage portion;
whereby the first blood transfer means is additionally adapted to facilitate the transfer of blood stored in the first storage portion to the second storage portion via the filtration device, and the second blood transfer means is additionally adapted to facilitate the transfer of the blood stored in the second storage portion to the first storage portion via the filtration device, characterised by a fluid measurement system, which is configured to: —periodically measure the respective volumes of blood in the first and second storage portions; add the measured volume of blood in the first storage portion to the measured volume of blood in the second storage portion at that time, in order to calculate the total volume of blood within the first and second storage portions at that time; and compare the total measured volumes of blood within the first and second storage portions measured over a predetermined time interval to calculate the volume of fluid removed from the blood of the patient during that predetermined time interval.

In this way, the total volume of fluid removed from the blood of the patient during an ultrafiltration process can be accurately measured. To elaborate, ultrafiltration is a process by which fluid is removed from the blood during the haemodialysis process. Normally, the amount of fluid removed is ascertained by means of measuring the total amount of dialysate fluid entering the dialysate circuit and comparing it with the total amount of dialysate fluid leaving the dialysate circuit, whereby the increase in the volume of the dialysate fluid leaving the dialysate circuit compared with its volume when it entered the dialysate circuit is equal to the total amount of fluid removed from the blood by means of the ultrafiltration process. Despite being a commonly used means for assessing the amount of fluid removed from the blood, this method suffers from the disadvantage that the errors in measurement associated with the various types of apparatus typically used to measure the amount of dialysate fluid entering and leaving the dialysate circuit can be high, sometimes being greater than the actual volume of fluid removed from the blood itself. By precisely measuring the volume of the blood directly, in accordance with the first aspect of the present invention, this provides a more accurate value for the amount of fluid removed from the blood during the ultrafiltration process.

Preferably, the fluid measurement system comprises a fluid control system for controlling the apparatus such that over a predetermined period of time, a predetermined volume of fluid is removed from the blood of the patient.

Preferably, the first blood transfer means comprises a first syringe having a first plunger defining a first chamber, and said second blood transfer means comprises a second syringe having a second plunger defining a second chamber.

Preferably, said fluid measurement system comprises a drive means for measuring and controlling the amount of blood in said first and second chambers of said first and second syringes respectively.

Preferably, said drive means comprises a first motor connected to a first means for measuring the distance moved by said first plunger as a result of the operation of said first motor, and a second motor connected to a second means for measuring the distance moved by said second plunger as a result of the operation of said second motor.

Preferably, said first and second means for measuring the distance moved by said first and second plungers respectively, are first and second discs having notches around their circumference.

This provides the advantage that the amount of blood in the apparatus and hence the amount of fluid removed from the blood, can be accurately measured and controlled.

In accordance with a second aspect of the present invention there is provided an apparatus for performing haemodialysis on a patient, said apparatus comprising: —
  (i) a filtration device through which the blood removed from the patient is passed in order to remove molecules from the blood;
  (ii) at least one fluid conduit for carrying fluid within said apparatus, wherein said fluid conduit is adapted to receive at least one flushing liquid that is drawn into said fluid conduit in an intake mode and expelled from said fluid conduit in a flushing mode and wherein, where the internal cross sectional area of said fluid conduit decreases as said flushing liquid flows in said flushing mode, said flow is substantially vertically upwards.

This provides the advantage that, in particular in those portions of the apparatus having a change in internal diameter, such as a stepped portion, the accumulation of air bubbles in the system, which can be harmful to the patient in the event that haemodialysed blood is returned to the patient, is substantially prevented. The reason for this is that, in relatively wide conduits, air bubbles naturally rise in a vertically upwards direction due to gravity, even against the flow of fluid. Accordingly, if, when the internal cross sectional area of said conduit decreases as said flushing liquid flows in said flushing mode (that is, the fluid conduit changes from being wider to narrower), said flow is substantially vertically upwards, then, as the bubbles naturally rise in a vertically upwards direction, they are flushed out of the apparatus. If this were not so, then air bubbles would be susceptible to accumulation in the apparatus, since they would not be flushed out by the fluid flow itself.

Accordingly, whilst appropriately controlling the pressure and flow in the apparatus, along with the disposition of the components of the apparatus, then in the event that air rises due to the effect of gravity, the air is flushed out of the apparatus.

Preferably, said fluid conduit is further adapted such that when said flow in said flushing mode is not substantially vertically upwards, said internal cross sectional diameter of said conduit is such that movement of any air in the fluid conduit is always with said flow of the flushing fluid.

Preferably, said fluid conduit is further adapted such that when said flow in said flushing mode is not substantially vertically upwards, said internal cross sectional diameter of said conduit is determined by factors including the density of the flushing liquid, the surface tension and viscosity of the flushing liquid, the length of the fluid conduit, the type of flushing fluid, the surface characteristics of the fluid conduit and the pressure within the apparatus during the flushing phase, so that movement of any air in the fluid conduit is with said flow of the flushing fluid.

Preferably, said fluid conduit is further adapted such that when said flow in said flushing mode is not substantially vertically upwards, said internal cross sectional diameter of said conduit is less than 1.7 mm.

Preferably, said fluid conduit is further adapted such that when said flow in said flushing mode is not substantially vertically upwards, said internal cross sectional diameter of said conduit is 1.5 mm.

In adapting said fluid conduit such that when said flow in said flushing mode is not substantially vertically upwards; that is, when said flow in said flushing mode is either substantially horizontal or is vertically downwards; said internal cross sectional diameter of said conduit is small enough such that movement of any air in the fluid conduit is with the flow of the flushing fluid; for example, 1.5 mm, this provides the advantage that the air bubbles tend to flow along with the fluid regardless of the orientation of the flow path; that is, regardless of whether the flow of fluid is substantially vertically upwards or not, with the result that the air is flushed out of the apparatus.

In accordance with a third aspect of the present invention there is provided an apparatus for performing haemodialysis on a patient, said apparatus comprising: —
  (i) a filtration device through which the blood removed from the patient is passed in order to remove molecules from the blood; and
  (ii) at least one fluid conduit for carrying fluid within said apparatus, wherein said fluid conduit is adapted to receive at least one flushing liquid that is drawn into said fluid conduit in an intake mode and expelled from said fluid conduit in a flushing mode and wherein, where said internal cross sectional diameter of said conduit is greater than that necessary to always facilitate movement of any air in the fluid conduit with said flow of the flushing fluid, said flow of flushing liquid in said flushing mode is substantially vertically upwards.

Accordingly, whilst appropriately controlling the pressure and flow in the apparatus, along with the careful selection of the internal diameters of fluid conduits connecting components of the apparatus together, air in the fluid conduit does not rise due to the effect of gravity even against the flow, but instead remains as a single portion of air moving in the direction of flow.

To elaborate, when expelling fluid from the apparatus during flushing, air is automatically removed from the apparatus by means of the arrangement of all components of the apparatus, such that: —(i) all components having internal diameters sufficient for discrete bubbles of air to move due to the effects of gravity will be disposed such that the direction of flow is vertically upwards; and (ii) selection of internal diameters of all other fluid conduits are such that air is moved in the direction of flow regardless of the effects of gravity.

In accordance with a fourth aspect of the present invention there is provided an apparatus for performing haemodialysis on a patient, said apparatus comprising: —
  (i) blood removal and return means for selectively withdrawing blood from and returning blood to, a patient; and
  (ii) a filtration device through which the blood removed from the patient is passed in order to remove molecules from the blood,
characterised in that the apparatus further comprises a pressure measurement and control system, which is adapted to: —

(a) periodically measure the pressure of the blood within the apparatus and increase or decrease the rate of return of blood to the patient as required in order to maintain the pressure of the blood within the apparatus substantially equal to a first predetermined value, in the event that blood is being returned to the patient; and (b) periodically measure the pressure of the blood within the apparatus and increase or decrease the rate of withdrawal of blood from the patient as required in order to maintain the pressure of the blood within the apparatus substantially equal to a second predetermined value, in the event that blood is being withdrawn from the patient.

It is to be appreciated that, when the blood is being withdrawn from the patient then the pressure of blood in the apparatus is negative. Similarly, when the blood is being returned to the patient then the pressure of blood in the apparatus is positive.

Preferably, said blood removal and return means comprises: —(i) first blood transfer means for selectively withdrawing blood from a patient and temporarily storing it in a first storage portion; and (ii) second blood transfer means for selectively removing filtered blood from the filtration device and temporarily storing it in a second storage portion, whereby the first blood transfer means is additionally adapted to facilitate the transfer of blood stored in the first storage portion to the second storage portion via the filtration device, and the second blood transfer means is additionally adapted to facilitate the transfer of blood stored in the second storage portion to the first storage portion via the filtration device.

Preferably, said pressure measurement and control system is adapted to measure said pressures relative to the patient.

Preferably, said pressure measurement and control system is active in the event that blood is being withdrawn from the patient and also when blood is being returned to the patient.

This provides the advantage that the patient is prevented from being subjected to pressures which are too negative in the event that blood is being withdrawn from the patient, and also, the patient is prevented from being subjected to positive pressures which are too high in the event that blood is being returned to the patient, both of which could be harmful to the patient. By way of example, in the event that the negative pressure of the blood becomes too negative, then the pressure measurement and control system reduces the rate of withdrawal of blood from the patient in order to bring the pressure to the second predetermined value once more. Conversely, in the event that the positive pressure of the blood becomes too high, then the pressure measurement and control system decreases the rate of return of blood to the patient in order to bring the pressure to the first predetermined value once more.

In this way, the pressure measurement and control system can employ a feedback loop to measure the pressure of the blood within the apparatus, and in the event that the pressure is required to be negative (i.e. during withdrawal of blood from the patient) but the pressure is below the second predetermined value, it will decrease the rate of withdrawal of blood from the patient by a decrement. At this point, the pressure of the blood within the apparatus is measured once again and if it is still below the second predetermined value, then the rate of withdrawal of blood from the patient is decreased once again by a further decrement. This continues until such times as the measured pressure of the blood within the apparatus reaches the second predetermined value, whereupon the rate of withdrawal of blood from the patient at that second predetermined value of the pressure, is maintained. However, the pressure continues to be measured periodically and the rate of withdrawal of blood from the patient altered when necessary, in order to maintain the pressure at the second predetermined value.

It is to be appreciated that as well as reducing the rate of withdrawal of the blood from the patient when necessary, as described above, the apparatus is additionally able to increase the rate of withdrawal of blood from the patient in the event that the rate of withdrawal of blood from the patient is reduced to such an extent that the negative pressure is above the second predetermined value.

In this way, the pressure measurement and control system controls the withdrawal rate so that the pressure is maintained at the second predetermined value.

However, it is also to be appreciated that if the pressure measured by the pressure measurement and control system does not actually drop below the second predetermined value, then the rate of withdrawal of blood from the patient is not altered in the way described above by the pressure measurement and control system such that the pressure is maintained at the second predetermined value. It is only when the measured pressure drops below the second predetermined value that the pressure measurement and control system hunts for and maintains, the second predetermined value of the pressure.

Moreover, the pressure measurement and control system can employ the feedback loop such that, in the event that the pressure is required to be positive (i.e. during return of blood to the patient) but the pressure exceeds the first predetermined value, it will decrease the rate of return of blood to the patient by a decrement. At this point, the pressure of the blood within the apparatus is measured once again and if it is still above the first predetermined value, then the rate of return of blood to the patient is decreased once again by a further decrement. This continues until such times as the measured pressure of the blood within the apparatus drops to the first predetermined value, whereupon the rate of return of blood to the patient at that first predetermined value of the pressure, is maintained. However, the pressure continues to be measured periodically and the rate of return of blood to the patient altered when necessary, in order to maintain the rate of return of blood to the patient at the value corresponding to the first predetermined value of the pressure.

It is to be appreciated that as well as reducing the rate of return of blood to the patient when necessary, as described above, the apparatus is additionally able to increase the rate of return of blood to the patient in the event that the rate of return of blood to the patient is reduced to such an extent that the pressure is lower than the first predetermined value.

In this way, the pressure measurement and control system controls the return rate so that the pressure is maintained at the first predetermined value.

However, it is also to be appreciated that if the pressure measured by the pressure measurement and control system does not actually exceed the first predetermined value, then the rate of return of blood to the patient is not altered in the way described above by the pressure measurement and control system such that the pressure is maintained at the first predetermined value. It is only when the measured pressure exceeds the first predetermined value that the pressure measurement and control system hunts for and maintains, the first predetermined value of the pressure.

Preferably, said first predetermined value of the pressure lies in the range between 100 and 350 mm of mercury.

Preferably, said second predetermined value of the pressure lies in the range between −100 and −350 mm of mercury.

It is to be appreciated that the values of first and second predetermined values of the pressure are selected bearing in mind that the patient should not be subjected to a pressure of too high magnitude (to prevent damage to blood) but also that realistically there will sometimes be some minor blockages throughout the apparatus.

Preferably, the pressure measurement and control system is further adapted to prevent the pressure of the blood within the apparatus from exceeding a third predetermined value, in the event that blood is being returned to the patient.

Preferably, said third predetermined value of the pressure is 400 mm of mercury.

This provides the advantage that damage to the blood of the patient as a result of being subjected to a pressure which is too positive (during return of blood to the patient), is prevented by means of the apparatus automatically shutting down in the event that the third predetermined value of the pressure is reached. In this way, the apparatus includes a further safety feature whereby if the maintenance of the pressure at the first predetermined value fails, then damage to the patient is further prevented by having a critical cut off point represented by the third predetermined value of the pressure, at which point the apparatus automatically shuts down as opposed to merely moderating the flow rate.

The third predetermined value of the pressure may be the pressure reached in the event that a portion of the apparatus becomes severely blocked, for example.

Preferably, the pressure measurement and control system is further adapted to prevent the pressure of the blood within the apparatus from dropping below a fourth predetermined value, in the event that blood is being withdrawn from the patient.

Preferably, said fourth predetermined value of the pressure is −400 mm of mercury.

This provides the advantage that damage to the blood of the patient as a result of being subjected to a pressure which is too negative (during withdrawal of blood from the patient), is prevented by means of the apparatus automatically shutting down in the event that the fourth predetermined value of the pressure is reached. In this way, the apparatus includes a further safety feature whereby if the maintenance of the pressure at the second predetermined value fails, then damage to the patient is further prevented by having a critical cut off point represented by the fourth predetermined value of the pressure, at which point the apparatus automatically shuts down as opposed to merely moderating the flow rate.

The fourth predetermined value of the pressure may be the pressure reached in the event that a portion of the apparatus becomes severely blocked, for example.

Preferably, the magnitude of the second predetermined value of the pressure is less than the magnitude of the fourth predetermined value of the pressure.

Preferably, the magnitude of the first predetermined value of the pressure is less than the magnitude of the third predetermined value of the pressure.

Preferably, the apparatus is further adapted to maintain the rate of withdrawal of blood from the patient at a fifth predetermined value.

Preferably, the apparatus is further adapted to maintain the rate of return of blood to the patient at a sixth predetermined value.

Preferably, the fifth predetermined value of the rate of withdrawal of blood is 20 ml min$^{-1}$ Preferably, the sixth predetermined value of the rate of return of blood is 20 ml min$^{-1}$ It is to be appreciated that the fifth and sixth predetermined values of the rate of withdrawal and return rates respectively, are optimal values.

The pressure measurement and control system may additionally be active in the event that blood is being passed through the filtration device.

BRIEF DESCRIPTION OF THE DRAWINGS

A preferred embodiment of the present invention will now be described, by way of example only and not in any limitative sense, with reference to the accompanying drawings in which: —

DETAILED DESCRIPTION

Figure 1:
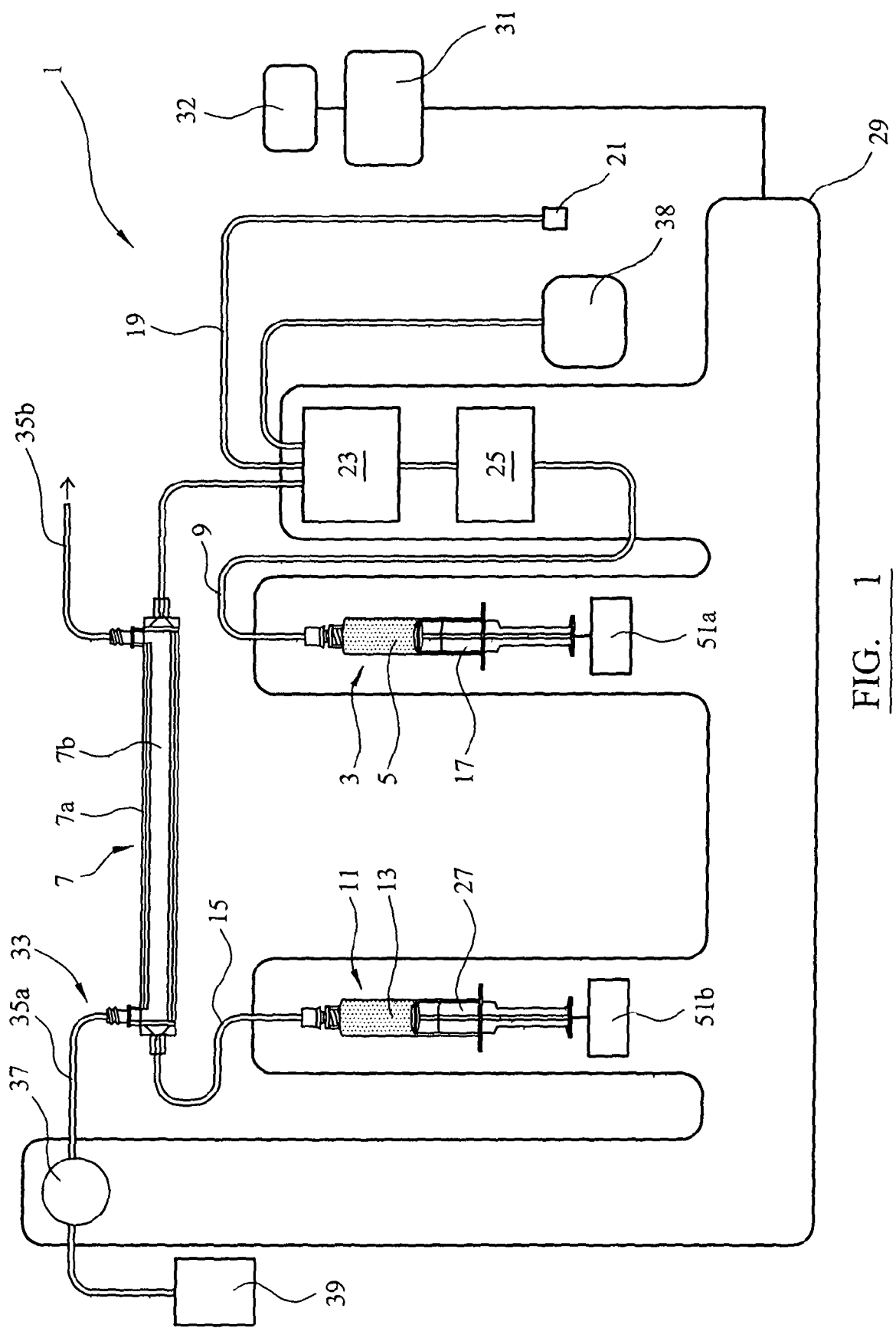
FIG. 1 shows a front view of an apparatus for performing haemodialysis on a neonate, in accordance with an embodiment of the present invention.

Referring to FIG. 1, an apparatus for performing haemodialysis on a neonate is represented generally by reference numeral 1.

It is to be appreciated that although the foregoing describes the operation of the invention as a means for haemodialysing a neonate, typically a neonate having a weight of 8 kg or under, it can be used in the haemodialysis of any suitable patient, for example, any baby who might feasibly be able to benefit from the apparatus 1.

The apparatus 1 comprises a first blood transfer means in the form of a first syringe 3 for selectively removing blood from a patient and temporarily storing it in a first storage portion in the form of a first chamber 5 of the first syringe 3.

The apparatus 1 further comprises a filtration device 7 comprising a hollow filtration tube 7a, which is divided into a first and a second portion separated from each other by a filtering material 7b such as polysulphone, whereby blood from the patient passes through the first portion and dialysate fluid (which will be discussed later) passes through the second portion. The filtration device 7 removes molecules which could otherwise harm the patient, from the blood by filtration and diffusion through the filtering material 7b.

The apparatus 1 further comprises a first hollow conduit in the form of a first tube 9 connecting the first syringe 3 and the filtration device 7. The first syringe 3 is connected to the first tube 9 by means of a first connector (not shown) at the upper end of the first syringe 3, with the result that the internal diameter experienced by the fluid flowing through the apparatus 1 decreases between the first syringe 3 and the first tube 9. The first syringe 3 is substantially vertically disposed.

The apparatus 1 further comprises a second blood transfer means in the form of a second syringe 11 for selectively removing filtered blood from the filtration device 7 and temporarily storing it in a second storage portion in the form of a second chamber 13 of the second syringe 11.

The apparatus further comprises a second hollow conduit in the form of a second tube 15 connecting the filtration device 7 and the second syringe 11. The second syringe 11 is connected to the second tube 15 by means of a second connector (not shown) at the upper end of the second syringe 11, with the result that the internal diameter experienced by the fluid flowing through the apparatus 1 decreases between the second syringe 11 and the second tube 15. The second syringe 11 is substantially vertically disposed.

It is to be appreciated that the first syringe 3 is additionally adapted to facilitate the transfer of blood between the first chamber 5 and the second chamber 13 via the first tube 9, the filtration device 7 and the second tube 15, respectively. Further, the second syringe 11 is additionally adapted to facilitate the transfer of blood between the second chamber 13 and the first chamber 5 via the second tube 15, the filtration device 7 and the first tube 9, respectively.

The apparatus 1 operates as follows: —

A first plunger 17 of the first syringe 3 is withdrawn from the first chamber 5 in order to withdraw blood from the patient via the patient access point 21 and the patient tube 19, and transfer it to the first chamber 5, where it is temporarily stored. In order to effect this withdrawal of blood from the patient, the valve mechanism 23 activates so that there is a continuous flow path for the blood between the patient access point 21 and the first chamber 5.

Once the first chamber 5 has been filled with blood, then the valve mechanism 23 activates to close off the flow path for the blood leaving the patient access point 21, resulting in a continuous flow path for the blood between the first chamber 5 and the filtration device 7, via the first tube 9. The first plunger 17 of the first syringe 3 then pushes the blood stored in the first chamber 5 vertically upwards and out of the first chamber 5, through the first tube 9 and into the filtration device 7, whereupon it is dialysed to remove molecules which may otherwise be harmful to the patient.

In tandem with the first syringe 3 pushing the blood through the first tube 9 as described above, the second syringe 11 effectively pulls the blood through the filtration device 7 via the second tube 15, as the second plunger 27 withdraws from the second chamber 13, thereby filling the second chamber 13 with blood.

Once the second chamber 13 has been filled with blood, then the second plunger 27 of the second syringe 11 pushes the blood stored in the second chamber 13 vertically upwards and out of the second chamber 13, through the second tube 15 and into the filtration device 7, whereupon it is dialysed once again, to remove molecules which may otherwise be harmful to the patient.

In tandem with the second syringe 11 pushing the blood through the second tube 15 as described above, the first syringe 3 effectively pulls the blood through the filtration device 7 via the first tube 9, as the first plunger 17 withdraws from the first chamber 5, thereby filling the first chamber 5 with blood once again.

This process may be repeated if necessary, until such times as the blood which has been removed from the patient has been adequately dialysed. Once this has been achieved then the valve mechanism 23 activates to close off the flow path for the blood between the first syringe 3 and the filtration device 7, resulting in a continuous flow path for the blood between the first chamber 5 and the patient access point 21. In this way, once the blood has been adequately dialysed, it is no longer circulated through the filtration portion of the apparatus 1 and is instead returned in its dialysed form, to the patient.

The apparatus 1 further comprises a circuit flushing portion 38, which is typically employed when the apparatus 1 is being flushed to remove air bubbles, before the blood is withdrawn from the patient. By way of example, in the event that the apparatus 1 is to be flushed, then the valve mechanism 23 activates to close off the flow path for the blood leaving the patient access point 21, resulting in a continuous flow path for fluid used to flush the apparatus 1, which can be saline for example, between the circuit flushing portion 38 and the first chamber 5 via the first tube 9.

The flushing of the apparatus is carried out in stages, with the first 3 and second 11 syringes being flushed separately and in sequence. In order to flush the first syringe 3, the first plunger 17 of the first syringe 3 is withdrawn from the first chamber 5 in order to transfer saline from the circuit flushing portion 38 into the first chamber 5, where it is temporarily stored.

Once the first chamber 5 has been filled with saline then the first plunger 17 pushes the saline back out of the first chamber 5 and out of the apparatus 1 via the first tube 9 and the circuit flushing portion 38, to be discarded.

Once the first syringe 3 has been flushed as described above, the valve mechanism 23 then activates to close off the flow path for the saline between the first chamber 5 and the circuit flushing portion 38, resulting in a continuous flow path for the saline between the second chamber 13 and the circuit flushing portion 38.

In order to flush the second syringe 11, the second plunger 27 of the second syringe 11 is withdrawn from the second chamber 13 in order to transfer saline from the circuit flushing portion 38 into the second chamber 13, where it is temporarily stored.

Once the second chamber 13 has been filled with saline then the second plunger 27 pushes the saline back out of the second chamber 13 and out of the apparatus 1 via the second tube 15 and the circuit flushing portion 38, to be discarded.

The feature of the first 3 and second 11 syringes being disposed such that as the saline leaves the syringes 3 and 11 and moves into the narrower first 9 and second 15 conduits respectively, during the respective flushing phases, the flow of the saline is vertically upwards. This ensures that any air bubbles are flushed out of the apparatus 1.

The first 9 and second 15 tubes have narrower internal diameters than, for example, the first 3 and second 11 syringes, since they have portions which are horizontally disposed. This ensures that air bubbles do not accumulate in the apparatus 1 during the flushing process, since the first 8 and second 15 tubes are narrow enough so that air moves through the tubes with the flow of the saline and does not rise due to gravity and become lodged in the apparatus 1.

The flushing of the first 3 and second 11 syringes can be repeated as required.

At this point, the apparatus 1 is now flushed and is ready to commence haemodialysis on the patient, as described previously.

The apparatus 1 further comprises a pressure measurement and control system 25, which is adapted to moderate the rate of withdrawal of blood and the rate of return of blood, to ensure that the pressure of the blood experienced by the patient is not at a level which would otherwise be harmful to the patient.

In the case where blood is being withdrawn from the patient, the rate of withdrawal is gradually increased from zero. Moreover, in the case where blood is being returned to the patient, the rate of return is gradually increased from zero.

The pressure measurement and control system 25 works on the basis that when blood is being withdrawn from the patient, the pressure of the blood within the apparatus is negative, and when blood is being returned to the patient, the pressure of the blood within the apparatus is positive.

Accordingly, the pressure measurement and control system 25 is adapted such that, when the blood is being returned to the patient (that is, when the pressure is positive), the pressure of the blood within the apparatus 1 is maintained at a first predetermined value. If the pressure exceeded the first predetermined value, this could result in damage to the patient by subjecting them to a pressure which is too positive. Further, when the blood is being withdrawn from the patient (that is, when the pressure is negative), the pressure of the blood within the apparatus 1 is maintained at a second predetermined value. If the pressure dropped below the second predetermined value, this could similarly result in damage to the patient by subjecting them to a pressure which is too negative.

In particular, in the event that blood is being withdrawn from the patient and the negative pressure of the blood within the apparatus 1 becomes too negative, then the pressure measurement and control system 25 reduces the rate of withdrawal of blood from the patient. Conversely, in the event that blood is being returned to the patient and the positive pressure of the blood within the apparatus 1 becomes too positive, then the pressure measurement and control system 25 reduces the rate of return of blood to the patient.

Taking first the example whereby the negative pressure measured by the pressure measurement and control system 25 falls below the second predetermined value, the pressure measurement and control system 25 periodically measures the pressure of the blood within the apparatus and increases and decreases the rate of withdrawal of blood from the patient as required, according to the measured pressure, in order to maintain the pressure of the blood within the apparatus substantially equal to the second predetermined value.

In this way, the pressure measurement and control system can employ a feedback loop to measure the pressure of the blood within the apparatus, and in the event that it is below the second predetermined value, decrease the rate of withdrawal of blood from the patient by a decrement. At this point, the pressure of the blood within the apparatus 1 is measured once again and if it is still below the second predetermined value, then the rate of withdrawal of blood from the patient is decreased once again by a further decrement. This continues until such times as the measured pressure of the blood within the apparatus 1 reaches the second predetermined value, whereupon the rate of withdrawal of blood from the patient at that second predetermined value of the pressure, is maintained. However, the pressure continues to be measured periodically and the rate of withdrawal of blood from the patient altered when necessary, in order to maintain the rate of withdrawal of blood from the patient at the value corresponding to the second predetermined value of the pressure.

It is to be appreciated that as well as reducing the rate of withdrawal of the blood from the patient when necessary, as described above, the apparatus 1 is additionally able to increase the rate of withdrawal of blood from the patient in the event that the rate of withdrawal of blood from the patient is increased to such an extent that the pressure is higher than the second predetermined value.

The pressure measurement and control system 25 is further adapted to prevent the pressure of the blood within the apparatus from dropping below a fourth predetermined value, in the event that the pressure of the blood in the apparatus 1 is required to be negative. In this way, the fourth predetermined value of the pressure is a critical safety cut off rate, whereby the apparatus 1 prevents the withdrawal rate from dropping below that value by means of automatically shutting down if the pressure becomes too negative to an extent that serious damage to the patient could otherwise occur.

The apparatus 1 is further adapted to gradually increase the rate of flow as the blood is being withdrawn from zero upon initiation of the apparatus 1 up to a sixth predetermined value, which is an optimal value and which is maintained once it has been reached. However, it is to be appreciated that if, as the rate of withdrawal is being increased from zero, the second predetermined value of the pressure is reached before the withdrawal rate has had the chance to reach the sixth predetermined value, then the rate of withdrawal is modified in as discussed above in order to maintain the pressure at the second predetermined value.

In this way, the pressure measurement and control system "hunts" for the second predetermined value of the pressure, whilst maintaining the rate of withdrawal of blood from the patient as close as possible to the optimum value of the withdrawal rate defined by the sixth predetermined value.

However, it is to be appreciated that if the pressure, which is measured periodically by the pressure measurement and control system 25 does not actually drop below the second predetermined value, then the rate of withdrawal of blood from the patient is not altered by the pressure measurement and control system 25 in the way described above and instead, the rate of withdrawal is gradually increased to the sixth predetermined value where it is maintained. The feedback loop is only employed in the event that the measured pressure falls below the second predetermined value.

Turning now to the situation whereby the positive pressure measured by the pressure measurement and control system 25 exceeds the first predetermined value, the pressure measurement and control system 25 periodically measures the pressure of the blood within the apparatus and increases and decreases the rate of return of blood to the patient as required, according to the measured pressure, in order to maintain the pressure of the blood within the apparatus substantially equal to the first predetermined value.

In this way, the pressure measurement and control system can employ a feedback loop to measure the pressure of the blood within the apparatus, and in the event that it is higher than the first predetermined value, decrease the rate of return of blood to the patient by a decrement. At this point, the pressure of the blood within the apparatus 1 is measured once again and if it is still higher than the first predetermined value, then the rate of return of blood to the patient is decreased once again by a further decrement. This continues until such times as the measured pressure of the blood within the apparatus 1 drops to the first predetermined value, whereupon the rate of return of blood to the patient at that first predetermined value of the pressure, is maintained. However, the pressure continues to be measured periodically and the rate of return of blood to the patient altered when necessary, in order to maintain the rate of return of blood to the patient at the value corresponding to the first predetermined value of the pressure.

It is to be appreciated that as well as reducing the rate of return of the blood to the patient when necessary, as described above, the apparatus 1 is additionally able to increase the rate of return of blood to the patient in the event that the rate of return of blood to the patient is increased to such an extent that the pressure is lower than the first predetermined value.

The pressure measurement and control system 25 is further adapted to prevent the pressure of the blood within the apparatus from exceeding a third predetermined value, in the event that the pressure of the blood in the apparatus 1 is required to be positive. In this way, the third predetermined value of the pressure is a critical safety cut off rate, whereby the apparatus 1 prevents the return rate from exceeding that value by means of automatically shutting down if the pressure becomes too positive to an extent that serious damage to the patient could otherwise occur.

The apparatus 1 is further adapted to gradually increase the rate of return from zero upon initiation of the apparatus 1 up to a fifth predetermined value, which is an optimal value and which is maintained once it has been reached. However, it is to be appreciated that if, as the rate of return is being increased from zero, the first predetermined value of the pressure is reached before the withdrawal rate has had the chance to reach the fifth predetermined value, then the rate of return is modified in as discussed above in order to maintain the pressure at the first predetermined value.

In this way, the pressure measurement and control system "hunts" for the first predetermined value of the pressure, whilst maintaining the rate of return of blood to the patient as close as possible to the optimum value of the rate of return of blood to the patient defined by the fifth predetermined value, without exceeding it.

However, it is to be appreciated that if the pressure, which is measured periodically by the pressure measurement and control system 25 does not actually exceed the first predetermined value, then the rate of return of blood to the patient is not altered by the pressure measurement and control system 25 in the way described above and instead, the rate of return is gradually increased to the fifth predetermined value where it is maintained. The feedback loop is only employed in the event that the measured pressure exceeds the first predetermined value.

The apparatus 1 further comprises a controller 29, which effectively controls the apparatus 1, in particular by driving the first 3 and second 11 syringes as required, and operating the valve mechanism 23 as required. To elaborate, the controller 29 controls the speed of the first 3 syringe in response to the pressure of the blood within the apparatus 1 as measured by the pressure measurement and control system 25, thereby altering the rate of withdrawal or return of blood from or to the patient, as required.

To elaborate, in the event that the rate of withdrawal of blood is to be increased, then the speed of the first syringe 3 is increased in the withdrawal direction; that is, the speed of withdrawal of the first plunger 17 is increased. Similarly, in the event that the rate of return of blood to the patient is to be increased, then the speed of the first syringe 3 is increased in the return direction; that is, the speed of movement of the first plunger 17 in an upwards direction so as to empty the first syringe 3, is increased.

Further, the controller 29 controls the relative speed of both the first 3 and second 11 syringes when controlling the ultrafiltration part of the process, in particular the rate of removal of fluid from the blood by the fluid measurement and control system, which will be described in further detail below.

The apparatus 1 further comprises a display 31, which provides the user with information concerning the apparatus 1. For example, the display 31 can present the user with information concerning the rate of withdrawal or return of blood from or to the patient and the measured pressure of the blood within the apparatus 1, at a particular time. The display 31 can also provide a representation of the apparatus 1 as a whole, for example, the real time positioning of the plungers 17 and 27, as well as the flow path being followed by the blood of the patient through the apparatus 1.

The apparatus 1 further comprises an input device 32 for setting the controller 29, for example, by inputting the appropriate predetermined values used throughout the haemodialysis process.

The apparatus 1 further comprises a dialysate circuit 33 for removing molecules from the blood of the patient by dialysis and filtration. The dialysate circuit 33 comprises a first dialysate tube 35$a$ for transferring dialysate fluid, which can be for example Accusol™, from a dialysate supply 39, into the filtration tube 7$a$, whereupon the molecules in the blood of the patient pass from the blood of the patient into the dialysate fluid across the polysulphone membrane 7$b$. The waste dialysate fluid then passes out of the filtration device 7 into a second dialysate tube 35$b$ whereupon it is disposed of. The dialysate circuit 33 further comprises a pump 37 which effectively transfers the dialysate fluid through the dialysate circuit 33. The controller 29 controls the operation of the pump 37 for pumping dialysate through the dialysate circuit 33.

It is to be appreciated that the apparatus 1 is disposed such that in the portion of the portion of the apparatus 1 defined by the first 3 and second 11 syringes, the fluid flow during the flushing phase follows a substantially vertically upwards path. The particular technical advantage associated with this feature is that the accumulation of air bubbles in the system is substantially reduced. To elaborate, air bubbles tend to rise with gravity in a vertically upwards direction in a fluid and so if the apparatus 1, in particular the syringes 3 and 11 and tubes used throughout the apparatus 1, are disposed such that the flow path of the fluid is vertically upwards in the event that there is a stepwise decrease in internal diameter as the fluid flows during the flushing phase, then the air bubbles, which can accumulate in the apparatus and naturally rise in a vertically upwards direction, would be more likely to be flushed out of the apparatus 1.

As well as removing molecules from the patient's blood by means of the haemodialysis process as described above, the apparatus 1 can perform an ultrafiltration function, in which water and waste products are removed from the blood. In order to achieve this, the relative speed of movement of the plungers 17 and 27 of the first 3 and second 11 syringes is varied such that the pressure inside the filtration device 7 increases such as to force fluid from the blood out through the filtering material 7$b$ as well as removing molecules by means of the haemodialysis process. To elaborate, if, as the blood of the patient is being passed from the first syringe 3 to the second syringe 11 via the dialysate circuit 33, the speed of the first syringe 3 in pushing the blood out of the first chamber is greater than that of the second syringe 11 pulling the blood into the second chamber, then fluid will be forced out of the blood and into the dialysate fluid.

Figure 2A:
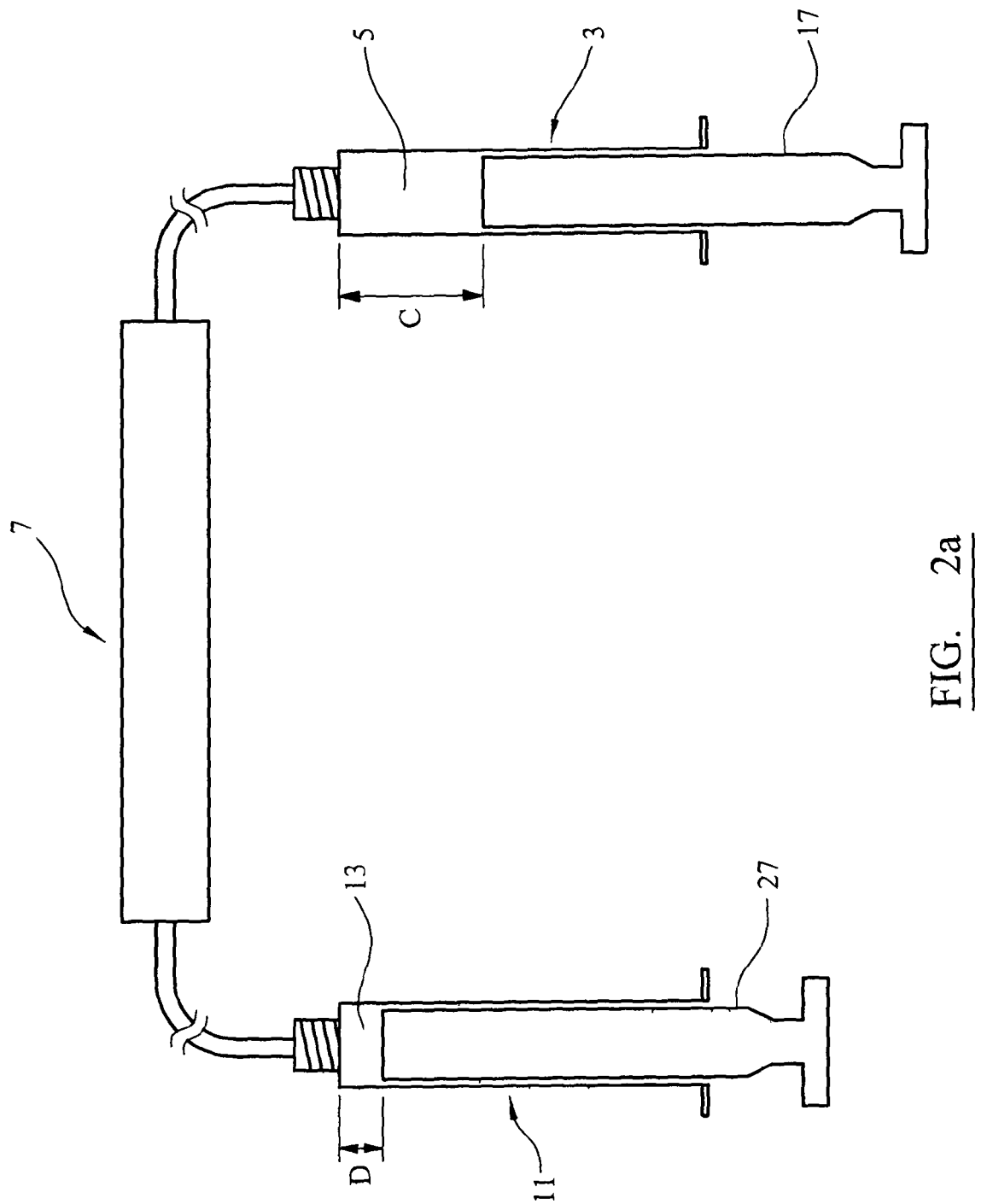
FIG. 2a is a schematic diagram showing a portion of the apparatus after the blood has been passed into the first syringe, illustrating the functionality of the fluid measurement and control system, in accordance with an embodiment of the present invention.
Figure 2B:
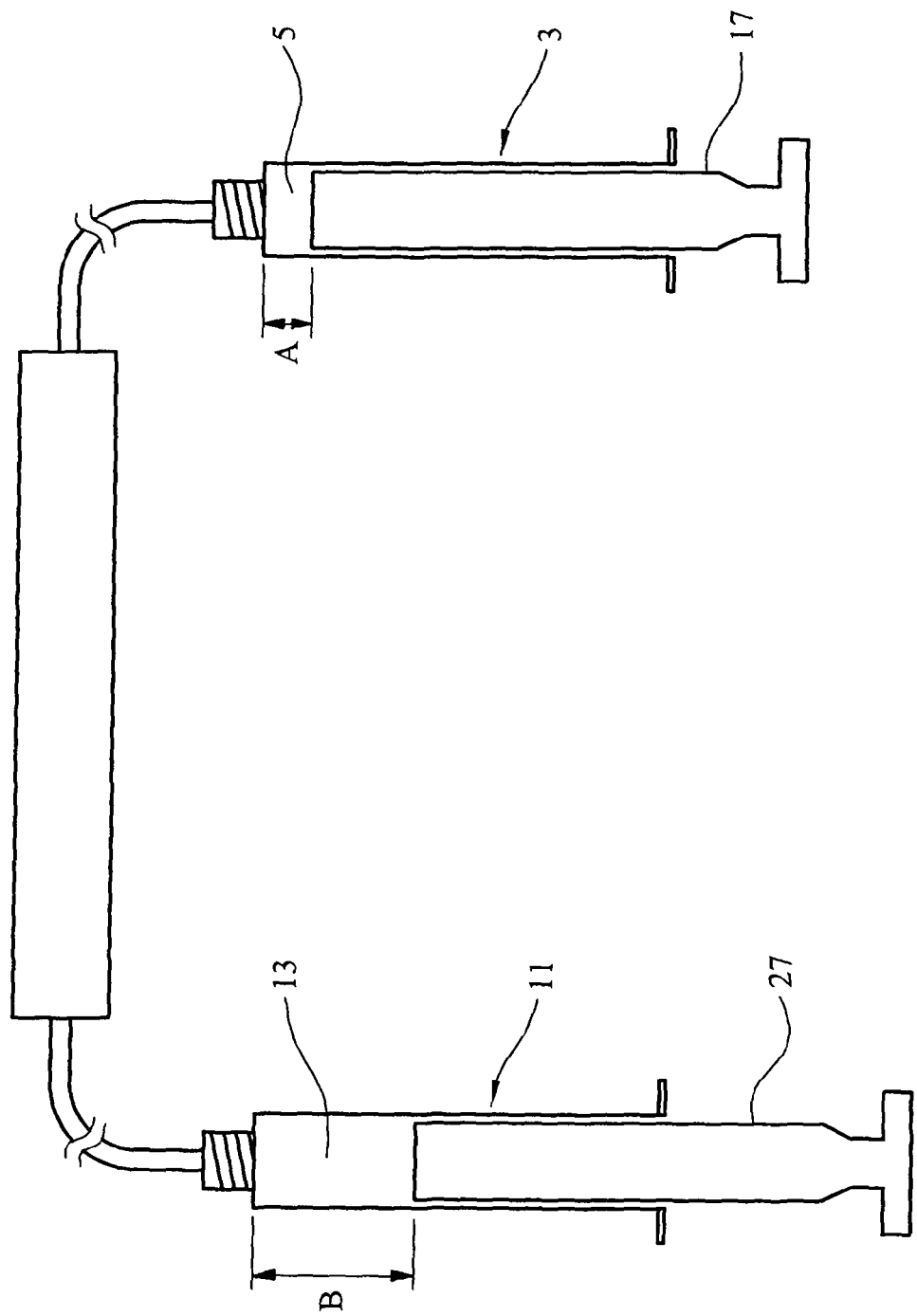
FIG. 2b is a schematic diagram showing a portion of the apparatus after the blood has been passed into the second syringe, illustrating the functionality of the fluid measurement and control system, in accordance with an embodiment of the present invention.

Turning now to FIGS. 1, 2$a$, 2$b$ and 3, a fluid measurement and control system 51$a$ and 51$b$ is shown, which periodically measures the volume of blood within the apparatus 1 as a measure of the amount of fluid, i.e. water, which has been removed from the blood as a result of the ultrafiltration process. By way of example, and with particular reference to FIG. 2b, when the blood has been transferred from the first syringe 3 into the second syringe 11 via the filtration device 7, the total amount of blood in the first 3 and second 11 syringes collectively is equal to Volume A+Volume B. Conversely, with particular reference to FIG. 2a, when the blood has then been transferred from the second syringe 11 back into the first syringe 3 via the filtration device 7, the total amount of blood in the first 3 and second 11 syringes collectively is equal to Volume C+Volume D. Typically, during the ultrafiltration process described above, the total volume of blood in the apparatus 1 would reduce after ultrafiltration cycles whereby the blood is passed through the filtration device 7 under pressure, since water will have been removed from the blood. Accordingly, the total reduction in blood volume, that is, the volume of fluid removed from the blood during the ultrafiltration process is (Volume A+Volume B)−(Volume C+Volume D).

In order to provide this measurement and therefore control of the volume of fluid removed from the blood, the first part 51a of the fluid measurement and control system comprises a first stepping motor assembly 100 operatively connected to the first syringe 3, and the second part 51b of the fluid measurement and control system comprises a second stepping motor assembly 162 operatively connected to the second syringe 11. The measurement and control of the volume of fluid removed from the blood can be achieved by working on the principle that the position of the first plunger 17 in the first syringe 3 directly relates to the volume of blood in the first syringe 3 at that time.

Similarly, the position of the second plunger 27 in the second syringe 11 directly relates to the volume of blood in the second syringe 11 at that time.

Figure 3:
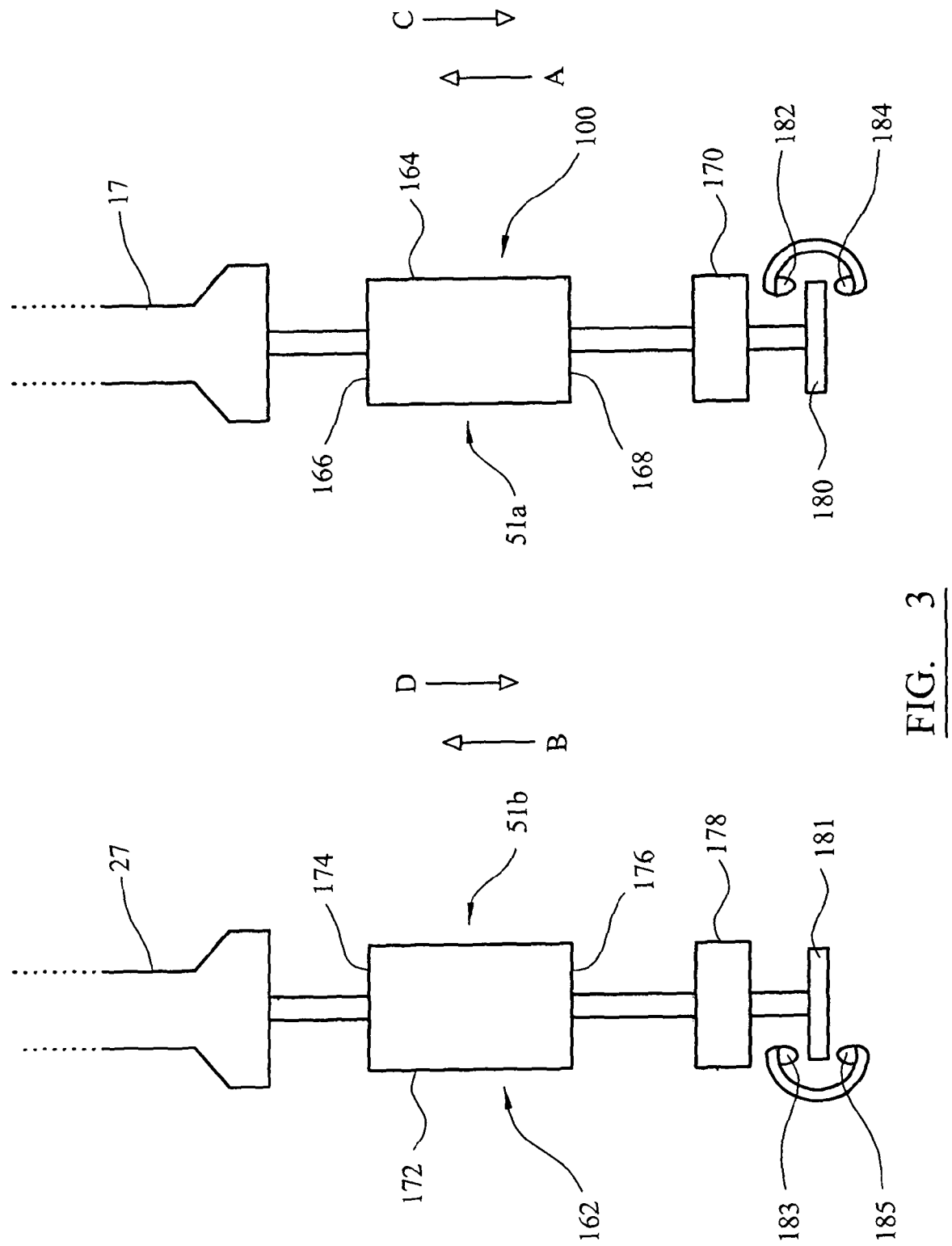
FIG. 3 shows a portion of the apparatus, illustrating the fluid measurement and control system, in accordance with an embodiment of the present invention.

The first stepping motor assembly 100 comprises a first rotatable gear 164 having a first end 166 and a second end 168. The first end 166 is attached to the rear of the first plunger 17 and the second end 168 is attached to a first motor 170. When the first motor 170 is actuated, the first rotatable gear 164 rotates and so advances in a forward direction; that is, in a direction indicated by the arrow A on FIG. 3. As a result of the first rotatable gear 164 advancing in a forward direction in this way, the first plunger 17 moves further inside the first chamber 5. In the event that the first motor 170 moves in an opposite direction, then the first rotatable gear 164 rotates in the opposite direction to before, and as a result, travels in the opposite direction, that is, in a direction indicated by the arrow C on FIG. 3. As a result of the first rotatable gear 164 moving in this opposite direction, the first plunger 17 moves out of the first chamber 5. In this way, the speed of the first syringe 3 can be controlled by means of controlling the speed of the first motor 170.

The movement of the first motor 170, hence the movement of the first plunger 17, which directly relates to the volume of blood in the first chamber 5, can be measured with the assistance of a first graduated disc 180 attached to the rear of the first motor 170. The first graduated disc 180 is graduated by means of notches formed at intervals around its circumference. A signal transmitter 182 is disposed to one side of the first graduated disc 180 and a signal receiver 184 is disposed to the opposite side of the first graduated disc 180 such that a signal is received by the signal receiver 184 as a notch passes the signal transmitter 182. In this way, the movement of the first rotatable gear 164 and hence the volume of blood in the first syringe 3 can be measured by measuring the number of signals received by the signal receiver 184 as the first graduated disc 180 rotates.

The second stepping motor assembly 162 comprises a second rotatable gear 172 having a first end 174 and a second end 176. The first end 174 is attached to the rear of the second plunger 27 and the second end 176 is attached to a second motor 178. When the second motor 178 is actuated, the second rotatable gear 172 rotates and so advances in a forward direction; that is, in a direction indicated by the arrow B on FIG. 3. As a result of the second rotatable gear 172 advancing in a forward direction, the second plunger 27 moves further inside the second chamber 13. In the event that the second motor 178 moves in an opposite direction, then the second rotatable gear 172 rotates in the opposite direction to before, and as a result, travels in the opposite direction, that is, in a direction indicated by the arrow D on FIG. 3. As a result of the second rotatable gear 172 moving in this opposite direction, the second plunger 27 moves out of the second chamber 13. In this way, the speed of the second syringe 11 can be controlled by means of controlling the speed of the second motor 178.

The movement of the second motor 178, hence the movement of the second plunger 27 and the volume of blood in the second chamber 13, can be measured with the assistance of a second graduated disc 181 attached to the rear of the second motor 178. The second disc 181 is graduated by means of notches formed at intervals around its circumference. A signal transmitter 183 is disposed to one side of the second graduated disc 181 and a signal receiver 185 is disposed to the opposite side of the second graduated disc 181 such that a signal is received by the signal receiver 185 as a notch passes the signal transmitter 183. In this way, the movement of the second rotatable gear 172 and hence the volume of blood in the second syringe 3 can be measured by measuring the number of signals received by the signal receiver 185 as the second graduated disc 181 rotates.

In this way, the amount by which the first 164 and second 172 rotatable gears rotate directly relates to the distance moved by the first 17 and second 27 plungers, which directly relates to the volume of blood within the first 5 and second 13 chambers respectively.

Accordingly, the first 164 and second 172 rotatable gears and hence the relative position of the first 17 and second 27 plungers can be moderated so that the first 5 and second 13 chambers of the first 3 and second 11 syringes respectively, each have a particular amount of blood disposed therein, and in this way, the amount of water and waste products removed from the blood; that is, the ultrafiltration process, can be accurately controlled and therefore measured.

The operation of the first 170 and second 178 motors is controlled by the controller 29.

It is also to be appreciated that the fluid flowing through the apparatus 1 follows a path having a substantially uniform internal diameter, having no stepped or bulbous portions, through the first 9 and second 15 tubes.

It is also to be appreciated that the first 9 and second 15 tubes have a narrow enough cross-sectional internal diameter such that any air bubbles present in the apparatus 1 follow the fluid flow during the flushing phase whatever its orientation (that is, vertically upwards, vertically downwards, horizontally or at any orientation inbetween). By means of example, the cross-sectional internal diameter of the first 9 and second 15 tubes is 1.5 mm.

It will be appreciated by persons skilled in the art that the above embodiments have been described by way of example only, and not in any limitative sense, and that various alterations and modifications are possible without departing from the scope of the invention as defined by the appended claims.

The invention claimed is:

1. A haemodialysis apparatus, said apparatus comprising:
   (i) a first blood transfer device including a first storage portion for selectively withdrawing blood from a patient and temporarily storing withdrawn blood in the first storage portion, the first storage portion including a first orifice for passage of the withdrawn blood into and out of said first storage portion;
   (ii) a filtration device through which said withdrawn blood is passed in order to remove molecules from the blood, whereby filtration of the blood by the filtration device results in haemodialysis;
   (iii) a second blood transfer device including a second storage portion for selectively removing filtered blood from the filtration device and temporarily storing the filtered blood in the second storage portion, the second storage portion having a second orifice for passage of the filtered blood into and out of said second storage portion;
   wherein the first blood transfer device facilitates transfer of the withdrawn blood stored in the first storage portion to the second storage portion through the filtration device, and the second blood transfer device facilitates transfer of the filtered blood stored in the second storage portion to the first storage portion through the filtration device, characterised by the apparatus further comprising a fluid measurement system, which is configured to:
   periodically measure respective volumes of blood in the first and second storage portions;
   add a measured volume of blood in the first storage portion to a measured volume of blood in the second storage portion at the time of the periodic measurement, in order to calculate a total volume of blood within the first and second storage portions at said time of said periodic measurement; and
   compare total measured volumes of blood within the first and second storage portions measured over a predetermined time interval to calculate a volume of fluid removed from the blood of the patient during the predetermined time interval;
   wherein:
   transfers of the withdrawn and filtered blood between the first and second storage portions are through the first and second orifices; and
   the apparatus further comprises a two-state valve mechanism arranged for selectively opening and closing a flow path between a patient access point and the first blood storage portion of the first blood transfer device, the two-state valve mechanism configured such that when in a first of the two states the flow path between the patient access point and the first storage portion of the first blood transfer device is closed such that there is no blood flow to or from the patient access point, and a fluid path between the first storage portion of the first blood transfer device and the filtration device, the filtration device, and the second storage portion of the second blood transfer device is opened and wherein the first state provides for the cycling of the filtered blood back and forth in opposite directions between the first and second storage portions of the first and second blood transfer devices across the filtration device, while the flow path between the patient access point and the first storage portion of the first blood transfer device is closed, wherein the blood is filtered by the filtration device each time the blood is transferred through the filtration device, and when in a second of the two states the flow path between the patient access point and the first storage portion of the first blood transfer device is opened, and the fluid path between the first storage portion of the first blood transfer device, the filtration device, and the second storage portion of the second blood transfer device is closed.

2. An apparatus as claimed in claim 1, wherein said fluid measurement system further comprises a fluid control system for controlling the apparatus such that over a predetermined period of time, a predetermined volume of fluid is removed from the blood of the patient.

3. An apparatus as claimed in claim 1, wherein the first blood transfer device comprises a first syringe having a first plunger defining a first chamber, and said second blood transfer device comprises a second syringe having a second plunger defining a second chamber.

4. An apparatus as claimed in claim 3, wherein said fluid measurement system further comprises a fluid control system for controlling the apparatus such that over a predetermined period of time, a predetermined volume of fluid is removed from the blood of the patient, and wherein said fluid measurement system comprises a drive means for measuring and controlling an amount of blood in said first and second chambers of said first and second syringes respectively.

5. An apparatus as claimed in claim 4, wherein said drive means comprises a first motor connected to a first means for measuring the distance moved by said first plunger as a result of operation of said first motor, and a second motor connected to a second means for measuring the distance moved by said second plunger as a result of the operation of said second motor.

6. An apparatus according to claim 1, wherein the first storage portion is comprised in the first blood transfer device and the second storage portion is comprised in the second blood transfer device.

7. An apparatus according to claim 4, wherein the drive means is configured to decrease the volume of the first fluid storage portion whilst increasing the volume of the second fluid storage portion and to decrease the volume of the second fluid storage portion whilst increasing the volume of the first fluid storage portion.

8. An apparatus according to claim 7, wherein the drive means is configured to cycle between decreasing and increasing the volume of the first fluid storage portion and increasing and decreasing the volume of the second fluid storage portion.

9. An apparatus according to claim 7, wherein the decrease in volume of the first fluid storage portion is greater than the increase in volume of the second fluid storage portion and the decrease in volume of the second fluid storage portion is greater than the increase in volume of the first fluid storage portion.

10. A haemodialysis apparatus, said apparatus comprising:
    a first syringe including a first storage portion for selectively withdrawing blood from a patient and temporarily storing withdrawn blood in the first storage portion, the first storage portion including a first orifice for passage of the withdrawn blood into and out of said first storage portion;
    a filtration device through which said withdrawn blood is passed in order to remove molecules from the blood, whereby filtration of the blood by the filtration device results in haemodialysis;
    a second syringe including a second storage portion for selectively removing filtered blood from the filtration device and temporarily storing the filtered blood in the second storage portion, the second storage portion having a second orifice for passage of the filtered blood into and out of said second storage portion;

wherein the first syringe facilitates transfer of the withdrawn blood stored in the first storage portion to the second storage portion through the filtration device, and the second syringe facilitates transfer of the filtered blood stored in the second storage portion to the first storage portion through the filtration device; and a two-state valve mechanism arranged for selectively opening and closing a flow path between a patient access point and the first blood storage portion of the first syringe, the two-state valve mechanism configured such that when in a first of the two states the flow path between the patient access point and the first storage portion of the first syringe is closed such that there is no blood flow to or from the patient access point, and a fluid path between the first storage portion of the first syringe and the filtration device, the filtration device, and the second storage portion of the second syringe is opened and wherein the first state provides for the cycling of the filtered blood back and forth in opposite directions between the first and second storage portions of the first and second syringes across the filtration device, while the flow path between the patient access point and the first storage portion of the first syringe is closed, wherein the blood is filtered by the filtration device each time the blood is transferred through the filtration device, and when in a second of the two states the flow path between the patient access point and the first storage portion of the first syringe is opened, and the fluid path between the first storage portion of the first syringe, the filtration device, and the second storage portion of the second syringe is closed.

* * * * *